(12) United States Patent
McDonald

(10) Patent No.: US 8,145,314 B2
(45) Date of Patent: Mar. 27, 2012

(54) SELF-SEALING SEPTUM ASSEMBLY

(75) Inventor: Matthew Lee McDonald, Glendale, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 445 days.

(21) Appl. No.: 12/410,674

(22) Filed: Mar. 25, 2009

(65) Prior Publication Data

US 2009/0248094 A1 Oct. 1, 2009

Related U.S. Application Data

(60) Provisional application No. 61/040,358, filed on Mar. 28, 2008.

(51) Int. Cl.
*A61N 1/00* (2006.01)

(52) U.S. Cl. .......................................................... 607/37

(58) Field of Classification Search .................. 607/37
See application file for complete search history.

(56) References Cited

U.S. PATENT DOCUMENTS

| | | | |
|---|---|---|---|
| 4,012,103 A | 3/1977 | Lunquist | |
| 4,479,489 A * | 10/1984 | Tucci | 607/37 |
| 4,496,348 A * | 1/1985 | Genese et al. | 604/167.02 |
| 4,915,960 A * | 4/1990 | Holmgren | 426/31 |
| 5,324,312 A | 6/1994 | Stokes et al. | |
| 5,433,734 A | 7/1995 | Stokes et al. | |
| 5,509,928 A | 4/1996 | Acken | |
| 5,766,042 A | 6/1998 | Ries et al. | |
| 5,906,634 A | 5/1999 | Flynn et al. | |
| 6,096,069 A | 8/2000 | Bischoff | |
| 6,205,358 B1 | 3/2001 | Haeg et al. | |
| 7,187,974 B2 | 3/2007 | Haeg et al. | |
| 7,231,253 B2 | 6/2007 | Tidemand et al. | |
| 7,445,528 B1 | 11/2008 | Kuzma et al. | |
| 2001/0034543 A1 | 10/2001 | Haeg et al. | |
| 2003/0040780 A1 | 2/2003 | Haeg et al. | |
| 2004/0122481 A1 | 6/2004 | Tidemand et al. | |
| 2009/0030475 A1 | 1/2009 | Brynelsen et al. | |

FOREIGN PATENT DOCUMENTS

| | | |
|---|---|---|
| WO | WO-9724779 | 7/1997 |
| WO | WO-2004009178 | 1/2004 |
| WO | WO-2009015150 | 1/2009 |

* cited by examiner

*Primary Examiner* — George Manuel
(74) *Attorney, Agent, or Firm* — Frommer Lawrence & Haug LLP; Bruce E. Black

(57) ABSTRACT

Exemplary septum assemblies include first and second housing components each defined by at least an inner surface, at least one sealing strip disposed at least partially on at least one of the inner surfaces of the housing components, and a compression member at least partially surrounding the housing components.

19 Claims, 6 Drawing Sheets

SELF-SEALING SEPTUM ASSEMBLY

CROSS REFERENCE TO RELATED APPLICATION

This application claims the benefit of U.S. Provisional Patent Application Ser. No. 61/040,358, filed Mar. 28, 2008, the entire contents of which is incorporated by reference.

BACKGROUND

Implantable stimulators are often used to treat a variety of medical disorders by providing electrical stimulation pulses via one or more electrodes placed at a desired stimulation site within a patient. The electrodes are typically disposed on one or more leads that are coupled to the implantable stimulator.

One type of implantable stimulator includes an implantable pulse generator (IPG) configured to provide spinal cord stimulation to a patient. At least one stimulating lead with one or more electrodes disposed thereon may be coupled to the IPG. In this manner, the lead may be implanted epidurally near the patient's spine and the IPG may be implanted in a surgically convenient location (e.g., within a subcutaneous pocket created within the torso of the patient). The IPG may then generate and deliver electrical stimulation pulses via the one or more electrodes to the spine in accordance with stimulation parameters configured to treat a particular medical disorder.

To facilitate coupling of a lead to an implantable stimulator, the stimulator may include a header assembly having a receptacle configured to receive a proximal portion of the lead. After the lead has been inserted into the receptacle, a set screw may be tightened against the lead to secure the lead in place.

However, it is often difficult to prevent body fluid and tissue ingress onto or around the set screw. These fluids and/or tissues may cause corrosion and/or premature failure of one or more components within the stimulator. They may also possibly prevent the set screw from being released in future procedures. In systems where the set screw is an active electrical element, fluid ingress may create accessory electrical current pathways that could reduce the effectiveness of the therapy provided by the stimulator or cause harm to the patient.

SUMMARY

Exemplary septum assemblies include first and second housing components each defined by at least an inner surface, at least one sealing strip disposed at least partially on at least one of the inner surfaces of the housing components, and a compression member at least partially surrounding the housing components.

Exemplary stimulators include a housing configured to house electronic circuitry configured to generate electrical stimulation, a receptacle at least partially disposed within the housing configured to receive a proximal portion of a lead, an orifice within the housing and having an opening in communication with an outer surface of the housing, the orifice being configured to receive a set screw, and a septum assembly coupled to the housing and configured to cover the opening of the orifice. The septum assembly includes first and second housing components each defined by at least an inner surface, at least one sealing strip disposed at least partially on at least one of the inner surfaces of the housing components, and a compression member at least partially surrounding the housing components. The at least one sealing strip is configured to create a seal over the opening of the orifice.

Exemplary systems include a stimulator having an orifice within a housing thereof and a septum assembly coupled to the stimulator and configured to cover an opening of the orifice. The septum assembly includes first and second housing components each defined by at least an inner surface, a first sealing strip disposed at least partially on the inner surface of the first housing component, a second sealing strip disposed at least partially on the inner surface of the second housing component, and a compression member at least partially surrounding the housing components. The first and second sealing strips are configured to create a seal over the opening of the orifice.

BRIEF DESCRIPTION OF THE DRAWINGS

The accompanying drawings illustrate various embodiments of the principles described herein and are a part of the specification. The illustrated embodiments are merely examples and do not limit the scope of the disclosure.

Throughout the drawings, identical reference numbers designate similar, but not necessarily identical, elements.

DETAILED DESCRIPTION

Systems, apparatuses, and methods for providing a reliable connection between an implantable stimulator and a lead coupled thereto are described herein. In some examples, a stimulator may be coupled to a header assembly, lead extension assembly, or other device having a receptacle disposed therein that is configured to receive a proximal portion of a lead. A hole configured to receive a set screw may also be disposed within the header assembly, lead extension assembly, or other device such that the set screw may be tightened with a wrench against the proximal portion of the lead.

In some examples, a self-sealing septum assembly may be configured to create a seal over an opening of the hole. The septum assembly may include first and second housing components each defined by at least an inner surface, a first sealing strip disposed at least partially on the inner surface of the first housing component, a second sealing strip disposed at least partially on the inner surface of the second housing component, and a compression member at least partially surrounding the housing components.

Upon insertion of a wrench in between the housing components, the wrench exerts a lateral force against the housing components. This lateral force causes the compression member to expand and the housing components to move away from one another. In this manner, the wrench may pass through the septum assembly and into the hole to tighten or loosen the set screw.

As will be described in more detail below, the septum assembly is configured to minimize damage to the sealing strips located in the inner surfaces of the housing components. Moreover, the septum assembly described herein is configured to prevent fluid and/or tissue ingress into the set screw hole such that a more reliable and secure connection may be made between the set screw and the lead.

In the following description, for purposes of explanation, numerous specific details are set forth in order to provide a thorough understanding of the present systems and apparatuses. It will be apparent, however, to one skilled in the art that the present systems and apparatuses may be practiced without these specific details. Reference in the specification to "one embodiment" or "an embodiment" means that a particular feature, structure, or characteristic described in connection with the embodiment is included in at least one embodiment. The appearance of the phrase "in one embodiment" in various places in the specification are not necessarily all referring to the same embodiment.

Figure 1:
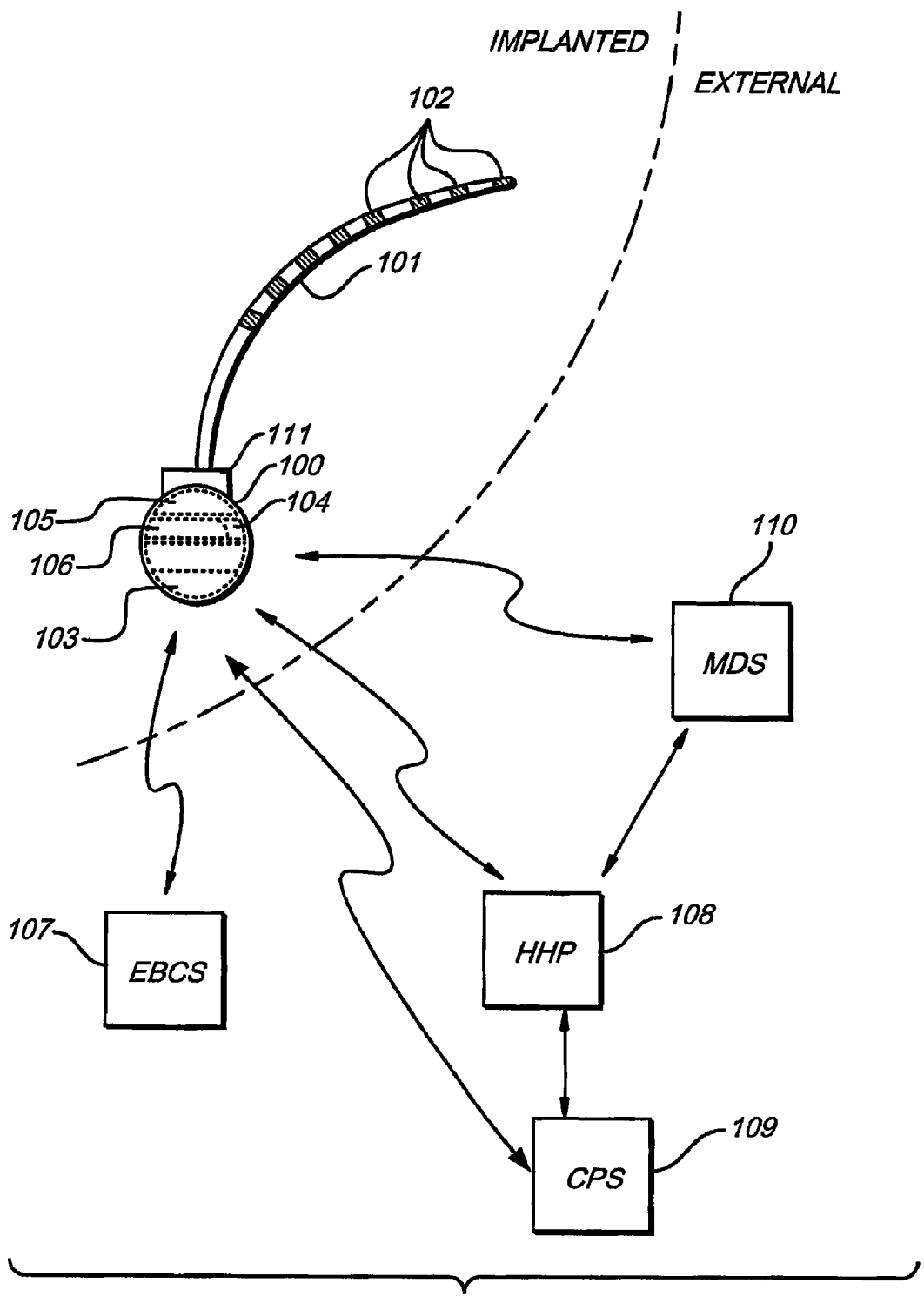
FIG. 1 illustrates an exemplary stimulator that may be used to apply electrical stimulation to one or more stimulation sites within a patient according to principles described herein.

To facilitate an understanding of the systems and methods described herein, a more detailed description of an implantable stimulator and its operation will now be given. FIG. 1 illustrates an exemplary stimulator 100 that may be used to apply electrical stimulation to one or more stimulation sites within a patient. The stimulation site may include any nerve or other tissue within the patient such as, but not limited to, a nerve within the spinal cord region, the heart, or any other location as may serve a particular application.

In some examples, the exemplary stimulator 100 shown in FIG. 1 may include at least one lead 101 coupled thereto. To this end, the stimulator 100 may include a header assembly 111 configured to facilitate coupling of the lead 101 to the stimulator 100. The header assembly 111 will be described in more detail below. Additionally or alternatively, the lead 101 may be coupled to the stimulator 100 via a lead extension.

In some examples, the at least one lead 101 includes a number of electrodes 102 through which electrical stimulation current may be applied to the stimulation site. It will be recognized that the at least one lead 101 may include any number of electrodes 102 arranged in any configuration as best serves a particular application. It will be recognized that the stimulator 100 may additionally or alternatively be coupled to one or more catheters through which one or more therapeutic drugs may be applied to the stimulation site.

As illustrated in FIG. 1, the stimulator 100 includes a number of components. For example, the stimulator 100 may include a power source 103, coil 104, electrical circuitry 105, and/or a programmable memory unit 106. It will be recognized that the stimulator 100 may include additional and/or alternative components as best serves a particular application.

The power source 103 is configured to output voltage used to supply the various components within the stimulator 100 with power and/or to generate the power used for electrical stimulation. The power source 103 may include a primary battery, a rechargeable battery (e.g., a lithium-ion battery), a super capacitor, a nuclear battery, a mechanical resonator, an infrared collector (receiving, e.g., infrared energy through the skin), a thermally-powered energy source (where, e.g., memory-shaped alloys exposed to a minimal temperature difference generate power), a flexural powered energy source (where a flexible section subject to flexural forces is part of the stimulator), a bioenergy power source (where a chemical reaction provides an energy source), a fuel cell, a bioelectrical cell (where two or more electrodes use tissue-generated potentials and currents to capture energy and convert it to useable power), or the like.

The coil 104 is configured to receive and/or emit a magnetic field (also referred to as a radio frequency (RF) field) that is used to communicate with, or receive power from, one or more external devices. Such communication and/or power transfer may include, but is not limited to, transcutaneously receiving data from the external device, transmitting data to the external device, and/or receiving power used to recharge the power source 103.

For example, an external battery charging system (EBCS) 107 may be provided to generate power that is used to recharge the power source 103 via any suitable communication link. Additional external devices including, but not limited to, a hand held programmer (HHP) 108, a clinician programming system (CPS) 109, and/or a manufacturing and diagnostic system (MDS) 110 may also be provided and configured to activate, deactivate, program, and/or test the stimulator 100 via one or more communication links. It will be recognized that the communication links shown in FIG. 1 may each include any type of link used to transmit data or energy, such as, but not limited to, an RF link, an infrared (IR) link, an optical link, a thermal link, or any other energy-coupling link.

Additionally, if multiple external devices are used in the treatment of a patient, there may be communication among those external devices, as well as with the implanted stimulator 100. It will be recognized that any suitable communication link may be used among the various devices illustrated.

The external devices shown in FIG. 1 are merely illustrative of the many different external devices that may be used in connection with the stimulator 100. Furthermore, it will be recognized that the functions performed by any two or more of the external devices shown in FIG. 1 may be performed by a single external device.

The stimulator 100 may also include electrical circuitry 105 configured to generate the electrical stimulation current that is delivered to the damaged neural tissue via one or more of the electrodes 102. For example, the electrical circuitry 105 may include one or more processors, capacitors, integrated circuits, resistors, coils, and/or any other component configured to generate electrical stimulation current.

The stimulator 100 may also include a programmable memory unit 106 configured to store one or more stimulation parameters. The programmable memory unit 106 allows a patient, clinician, or other user of the stimulator 100 to adjust the stimulation parameters such that the stimulation applied by the stimulator 100 is safe and effective in treating a particular patient. The programmable memory unit 106 may include any type of memory unit such as, but not limited to, random access memory (RAM), static RAM (SRAM), a hard drive, or the like.

The stimulator 100 of FIG. 1 is illustrative of many types of stimulators that may be used in accordance with the systems and methods described herein. For example, the stimulator 100 may include an implantable pulse generator (IPG), a microstimulator, a pacemaker, a defibrillator, an external trial stimulator, and/or any other type of device configured to deliver electrical stimulation to a stimulation site within a patient.

Figure 2:
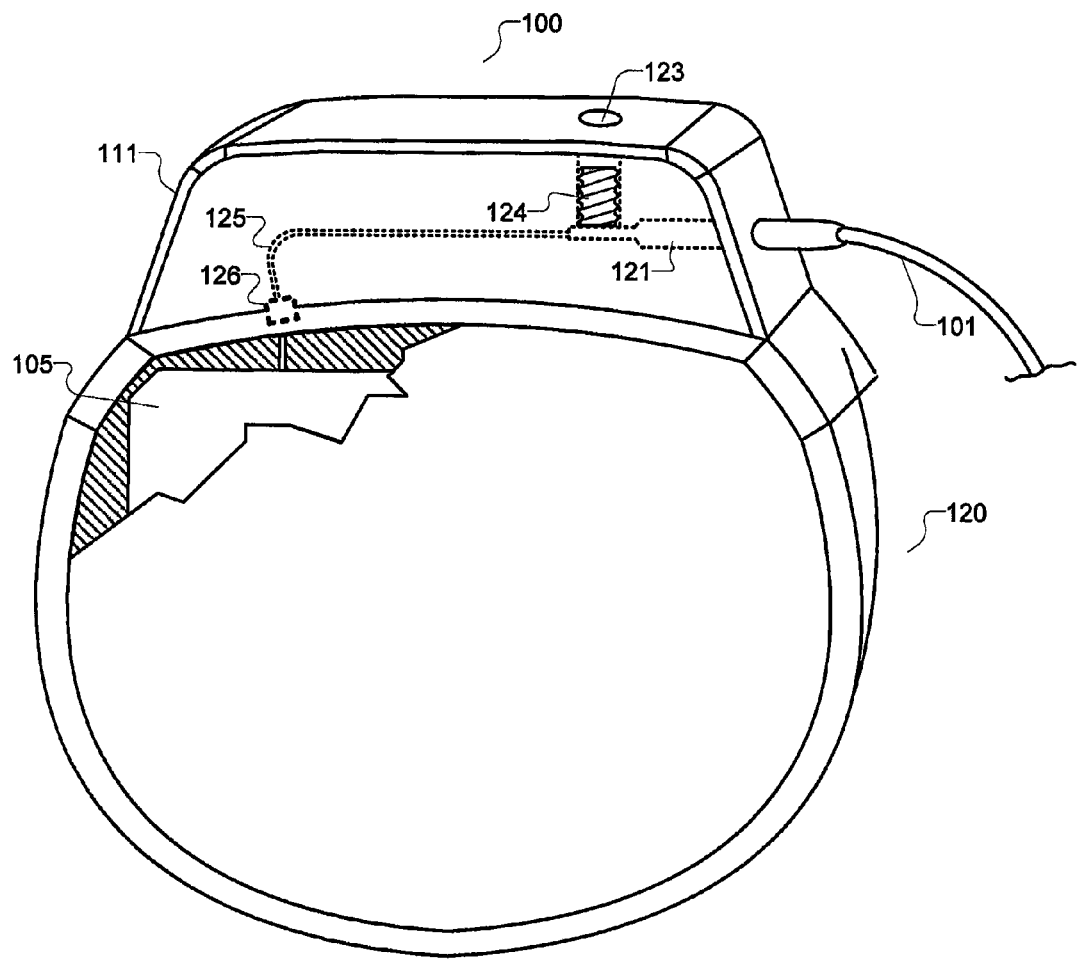
FIG. 2 is a perspective view of a stimulator and a header assembly according to principles described herein.

FIG. 2 is a perspective view of the stimulator 100 of FIG. 1 and illustrates the header assembly 111 in more detail. In some examples, the header assembly 111 is configured to facilitate coupling of the lead 101 to the stimulator 100. While a header assembly 111 is shown in FIG. 2, the lead 101 may alternatively be coupled directly to the stimulator 100 or coupled to the stimulator 100 using a lead extension assembly.

As shown in FIG. 2, the stimulator 100 may include a main housing 120 configured to house one or more components of the stimulator 100. For example, the housing 120 may be configured to house the power source 103, coil 104, electrical circuitry 105, and/or programmable memory unit 106. To this end, the housing 120 may include, but is not limited to, a hermetic encasing configured to prevent entry therein of bodily fluids. The housing 120 may be made out of any suitable material including, but not limited to, metal, metal alloys, ceramics, plastics, polymers, and/or combinations thereof.

The header assembly 111 may be hermetically coupled to the main housing 120, as shown in FIG. 2. The header assembly 111 may be made out of any suitable material as may serve a particular application. For example, the header assembly 111 may be made out of metal, metal alloys, ceramics, plastics, polymers, and/or combinations thereof.

To facilitate electrical coupling of a lead 101 to the electrical circuitry 105 housed within the housing 120, the header assembly 111 may include a receptacle 121 dimensioned to receive a proximal portion of the lead 101. An electrical conductor 125 (e.g., one or more conductive wires) may be coupled to the receptacle 121 at one end and to a feedthrough assembly 126. The feedthrough assembly 126 is electrically coupled to the electrical circuitry 105 within the housing 120.

The surface defining the receptacle 121 may include at least one conductive portion configured to maintain electrical contact with the proximal portion of the lead 101 when the lead 101 is inserted within the receptacle 121. To this end, the proximal portion of the lead 101 may include a conductive connector pin and/or one or more conductive contacts disposed thereon configured to be in physical contact with the conductive portion of the receptacle 121.

In some examples, the header assembly 111 may include a threaded hole or orifice 123 extending substantially perpendicular from the receptacle 121 to the outer surface of the header assembly 111. It will be recognized that the hole 123 may alternatively extend from the receptacle 121 at any suitable angle. The threaded hole 123 is configured to receive a set screw 124. The set screw 124 may be screwed down within the threaded hole 123 until contact is made with the proximal portion of the lead 101. In this manner, a secure mechanical connection may be maintained between the header assembly 111 and the lead 101. In some examples, an electrical connection may additionally be made between the set screw 124 and the lead 101 when the set screw 124 is in contact with the proximal portion of the lead 101. To remove the lead 101 from the header assembly 111, the set screw 124 may be loosened.

As mentioned, it is often difficult to prevent body fluid and tissue ingress onto or around the connection made between the set screw 124 and the inserted lead 101. These fluids and/or tissues may cause corrosion and/or premature failure of one or more components within the stimulator 100. In systems where the set screw 124 is an active electrical element, fluid ingress may create accessory electrical current pathways that could reduce the effectiveness of the therapy provided by the stimulator 100 or cause harm to the patient.

To this end, the header assembly 111 may include a self-sealing septum assembly 130 (or simply "septum assembly 130") configured to prevent fluid and tissue ingress into or around the connection made between the set screw 124 and the inserted lead 101. As will be described in more detail below, the septum assembly 130 may be configured to create a seal over the opening of hole 123 to prevent fluid and tissue ingress into the hole 123. At the same time, the septum assembly 130 is configured to allow passage therethrough of a wrench to tighten or loosen the set screw 124 disposed within the hole 123.

Figure 3A:
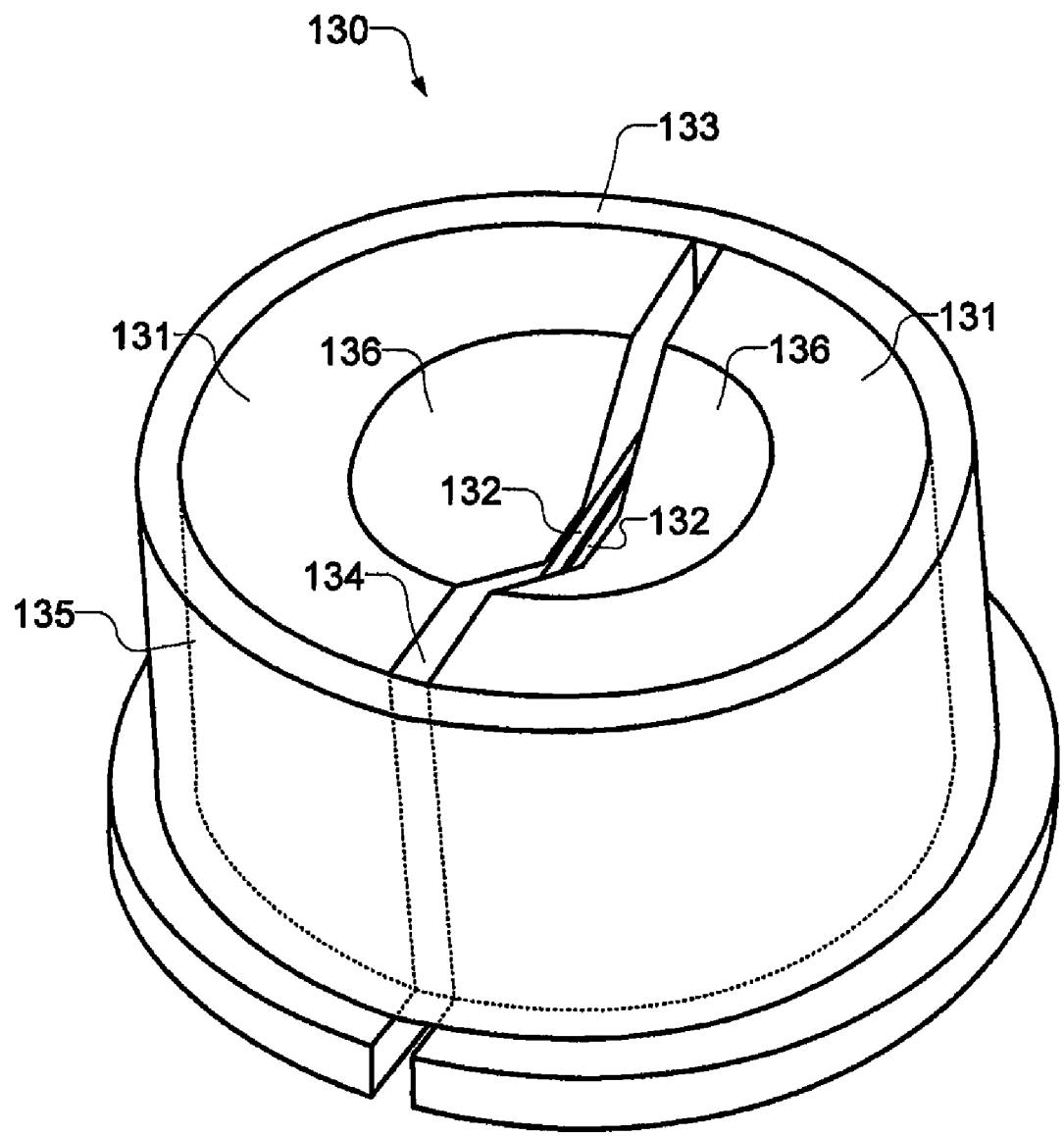
FIG. 3A is a perspective view of an exemplary self-sealing septum assembly in a closed state according to principles described herein.
Figure 3B:
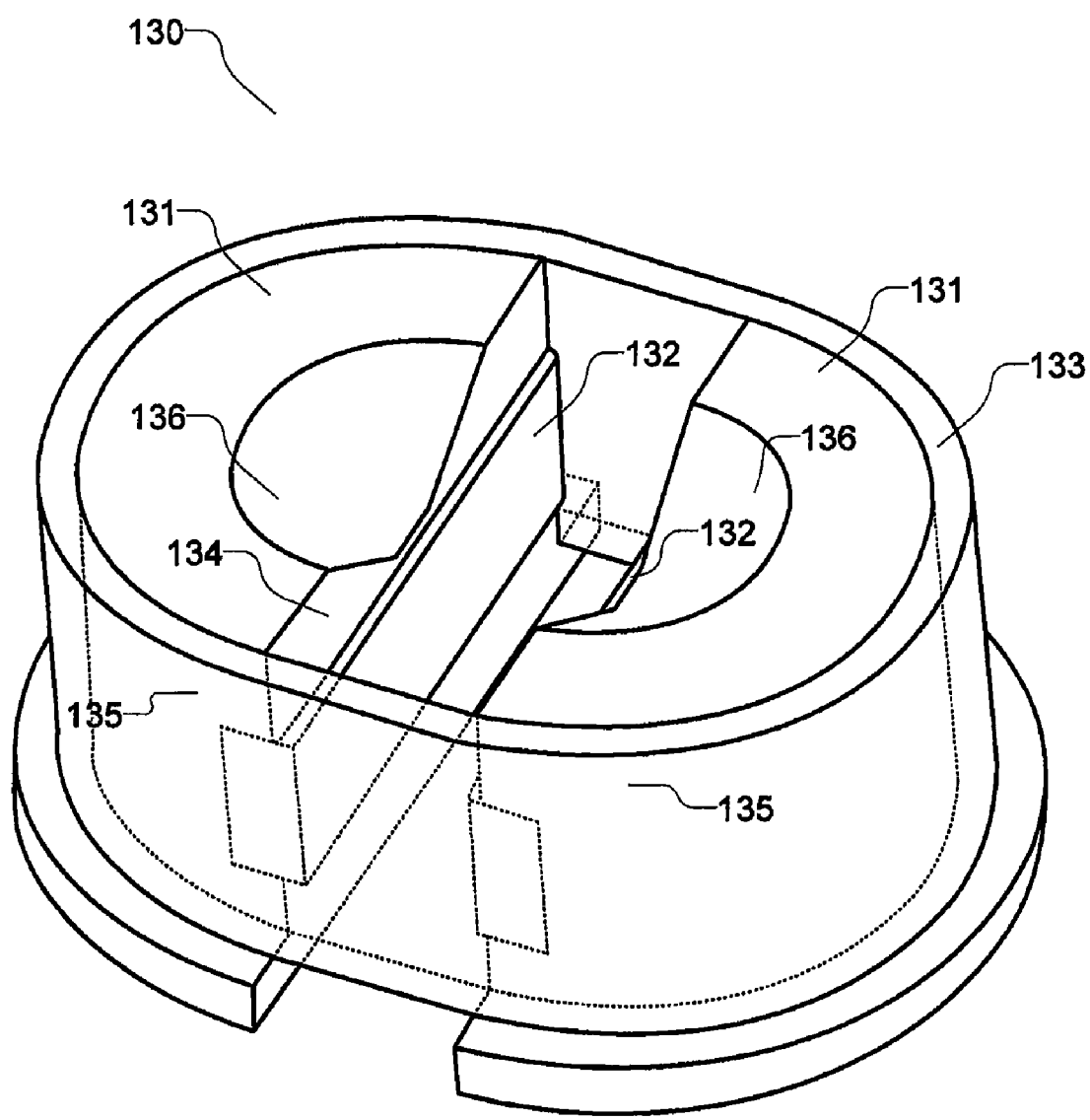
FIG. 3B is a perspective view of the exemplary self-sealing septum assembly of FIG. 3A in an open state according to principles described herein.

FIG. 3A is a perspective view of an exemplary septum assembly 130 in a closed state that may be used in accordance with the systems and methods described herein. FIG. 3B shows the septum assembly 130 of FIG. 3A in an open state. As shown in FIGS. 3A-3B, the septum assembly 130 may include first and second housing components 131-1 and 131-2 (collectively referred to as housing components 131), first and second sealing strips 132-1 and 132-2 (collectively referred to as sealing strips 132) disposed on an inner surface of the housing components 131, and a compression member 133 surrounding the housing components 131. Each of these components will be described in more detail below.

As shown in FIG. 3A, the septum assembly 130 may be cylindrically shaped with each housing component 131 in the form of a half cylinder. Hence, each housing component 131 may be defined by a planar inner surface 134 and a curved outer surface 135. It will be recognized that the housing components 131 may be of any suitable shape and size as may serve a particular application. For example, each of the housing components 131 may be generally rectangular.

In some examples, the housing components 131 may each be made of a generally rigid material. Such materials may include, but are not limited to, plastic, metal, metal alloys, and the like. As will be described in more detail below, the rigidity of the housing components 131 may serve to protect the sealing strips 133 from exposure and/or damage caused by a wrench being inserted into the septum assembly 130.

To aid in the alignment of a wrench with the set screw 124, each of the housing components 131 may include a tapered portion 136 configured to guide the wrench into the hole 123 of the header assembly 111. Insertion of the wrench into the hole 123 will be described in more detail below.

As shown in FIGS. 3A-3B, a sealing strip 132 may be coupled to an inner surface 134 of one or more of the housing components 131. In some examples, each sealing strip 132 is configured to extend along the entire length of the inner surface 134 of its corresponding housing component 131 and wrap at least partially around the curved outer surface 135 of the corresponding housing component 131. Alternatively, each sealing strip 132 may only partially extend along the inner surface 134 of its corresponding housing component 131. It will be recognized that two sealing strips 132 are shown in FIGS. 3A-3B for illustrative purposes and that one sealing strip 132 or more than two sealing strips 132 may alternatively be included as may serve a particular application.

In some examples, the sealing strips 132 are configured to create a seal over the hole 123 of the header assembly 111 when pressed against each other. To this end, the sealing strips 132 may be made out of any suitable material configured to create a seal when pressed against each other. For example, the sealing strips 132 may be made out of silicone or any other suitable material.

As shown in FIGS. 3A-3B, the compression member 133 is configured to surround the housing components 131. In its natural state (i.e., in the closed state shown in FIG. 3A), the compression member 133 is configured to exert a compressive force on the housing components 131 such that the sealing strips 132 are pressed against each other to create a seal. As will be described in more detail below, insertion of a wrench into the septum assembly 130 causes the compression member 133 to expand (i.e., to the open state shown in FIG. 3B), thereby allowing the housing components 131 to move away from each other and create a passage way for the wrench into the hole 123. When the wrench is removed from the septum assembly 130, the compression member 133 resumes its compressed state in order to maintain the seal.

Hence, the compression member 133 may made out of any elastic material such as, but not limited to, silicon, rubber, and/or combinations or derivatives thereof. Additionally, the composition of the compression member 133 may be such that it may be stretched sufficiently to allow full insertion of a wrench in between the housing components 131 of the septum assembly 130 as well as resilient enough to provide a sufficient returning force to press the sealing strips 131 against each other to create a seal over the hole 123 of the header assembly 111 when the wrench is removed.

The compression member 133 may vary in thickness as may suit a particular application. For example, the compression member 133 may include a relatively thin compression band, as shown in FIGS. 3A-3B. In some alternative embodiments, the compression member 133 may include a relatively thick body of silicone in which the housing components 131 are disposed. In these embodiments, the compression member 133 may facilitate separation of the housing components 131 through the displacement of various portions of the body of silicone from one region to another. The silicone body may be an integrally molded part of the stimulator 100, for example.

Figure 4A:
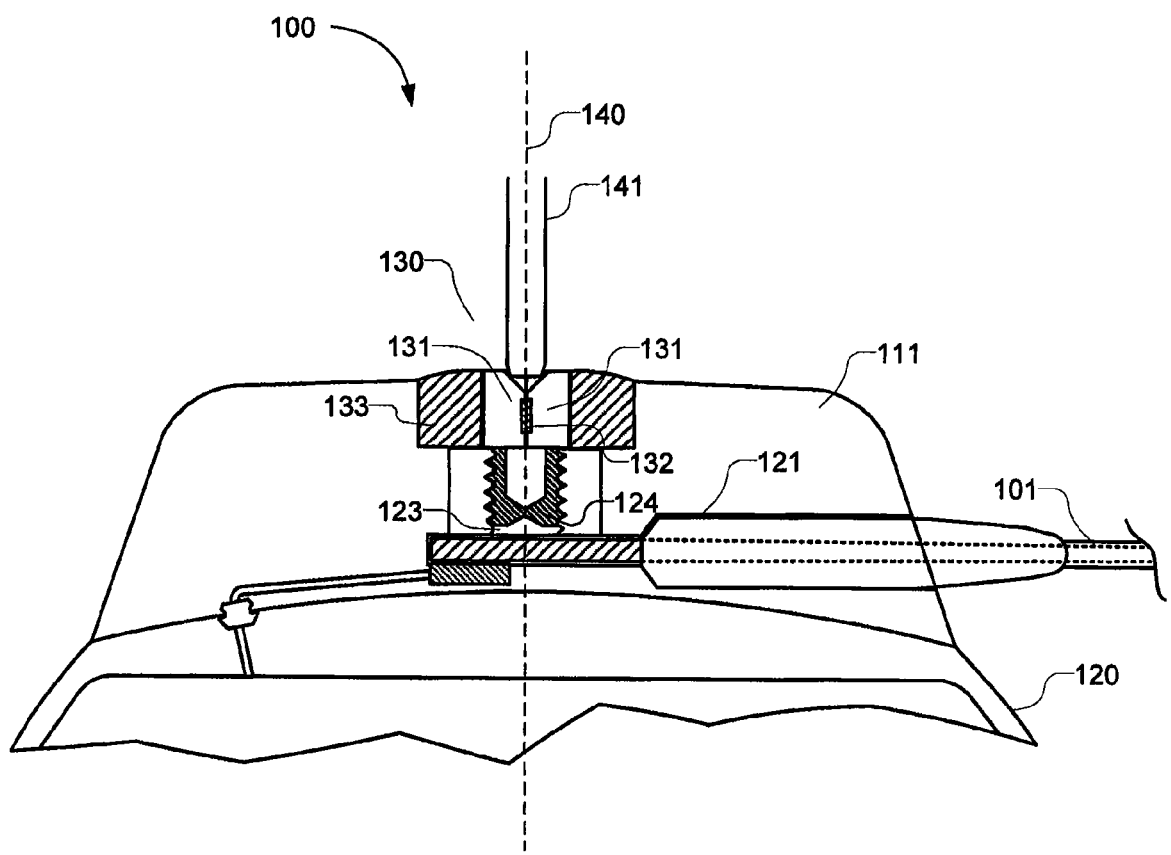
FIG. 4A is a cross sectional side view of a header assembly with a septum assembly disposed therein according to principles described herein.

An illustrative application of the septum assembly 130 will be described in connection with FIGS. 4A-4B. FIG. 4A is a cross sectional side view of the header assembly 111 with the septum assembly 130 included therein. As shown in FIG. 4A, a central axis of the septum assembly (represented in FIGS. 4A-4B by dashed line 140) is aligned with a central axis of the hole 123. The sealing strips 132 may extend in a direction generally perpendicular to the central axis 140.

When a wrench 141 is inserted into the septum assembly 130 along the central axis 140, the wrench 141 exerts a lateral force against the housing components 131. This lateral force causes the housing components 131 to move away from one another so that the wrench may pass through the septum assembly 130 and into the hole 123.

Figure 4B:
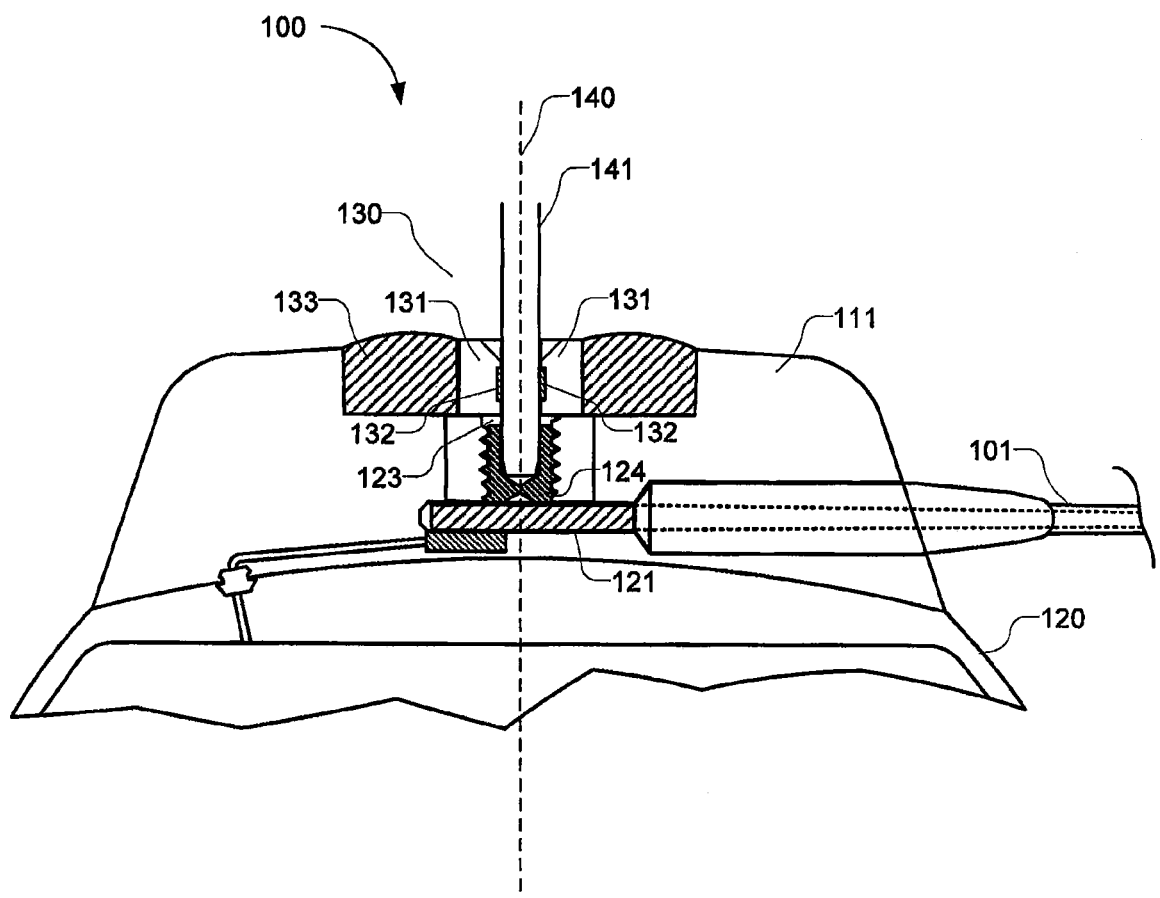
FIG. 4B is another cross sectional side view of the header assembly of FIG. 4A according to principles described herein.

FIG. 4B shows the header assembly 111 and septum assembly 130 of FIG. 4A after the wrench 141 has passed in between the housing components 131 and into the hole 123. As shown in FIG. 4B, the wrench is engaged with the set screw 124. A user may then tighten or loosen the set screw as desired with the wrench 141.

For example, a user may tighten the set screw 124 to secure the proximal portion of a lead 101 within the receptacle 121. To remove the lead 101 from the receptacle 121, the user may loosen the set screw 124. In some examples, the bottom surface of the housing components 131 may be configured to serve as a stop that prevents over loosening of the set screw 124. In this manner, removal of the set screw 124 from the hole 123 may be prevented.

It will be recognized that the wrench 141 shown in FIGS. 4A-4B may include any device as may serve a particular application. For example, the wrench 141 may include an Allen wrench, a screw driver, a star key, a square key, a hexagonal key, and/or variations thereof.

Upon removal of the wrench from the hole 123 and septum assembly 130, the compression force exerted by the compression member 133 pushes the housing components 131 together until the sealing strips 132 reform a seal over the hole 123.

The preceding description has been presented only to illustrate and describe embodiments of the invention. It is not intended to be exhaustive or to limit the invention to any precise form disclosed. Many modifications and variations are possible in light of the above teaching.

What is claimed is:

1. A septum assembly comprising:
   first and second housing components each defining at least an inner surface, wherein said housing components are made of a generally rigid material and the inner surfaces of the first and second housing components oppose each other;
   at least one sealing strip disposed at least partially on each of said inner surfaces of said housing components; and
   a compression member at least partially surrounding said housing components, wherein the compression member is configured and arranged to expand in response to a tool inserted between the first and second housing components to further separate the first and second housing components.

2. The septum assembly of claim 1, wherein:
   said compression member is configured to exert a force on said first and second housing components such that said sealing strips create a seal between said inner surfaces of said housing components.

3. The septum assembly of claim 1, wherein said sealing strips are made of a silicone material.

4. The septum assembly of claim 1, wherein said compression member is made of an elastic material.

5. The septum assembly of claim 1, wherein each of said housing components is further defined by a curved outer surface, and wherein said sealing strips extend at least partially along one or more of said curved outer surfaces.

6. The septum assembly of claim 1, wherein at least one of said housing components comprises a tapered portion configured to guide a wrench in between said first and second housing components.

7. The septum assembly of claim 1, wherein said sealing strips comprise:
   a first sealing strip disposed at least partially on said inner surface of said first housing component; and
   a second sealing strip disposed at least partially on said inner surface of said second housing component.

8. The septum assembly of claim 1, wherein said compression member comprises at least one of a compression band or a silicone body integrally molded into a stimulator.

9. The septum assembly of claim 1, wherein said first and second housing components are configured to serve as a stop to prevent over loosening of a set screw.

10. A stimulator comprising:
    a housing configured to house electronic circuitry configured to generate electrical stimulation;
    a receptacle at least partially disposed within said housing configured to receive a proximal portion of a lead;
    an orifice within said housing and having an opening in communication with an outer surface of said housing, said orifice being configured to receive a set screw, said set screw configured to be tightened against said proximal portion of said lead; and
    a septum assembly coupled to said housing and configured to cover said opening of said orifice;
    wherein said septum assembly comprises
    first and second housing components each defining at least an inner surface, wherein said housing components are made of a generally rigid material and the inner surfaces of the first and second housing components oppose each other,
    at least one sealing strip disposed at least partially on each of said inner surfaces of said housing components, and a compression member at least partially surrounding said housing components, wherein the compression member is configured and arranged to expand in response to a tool inserted between the first and second housing components to further separate the first and second housing components;

wherein said sealing strips are configured to create a seal over said opening of said orifice.

11. The stimulator of claim 10, wherein said compression member is configured to exert a force on said first and second housing components such that said sealing strips create said seal.

12. The stimulator of claim 10, wherein said housing components are configured to prevent over loosening of said set screw within said orifice.

13. The stimulator of claim 10, wherein said sealing strips are made of a silicone material.

14. The stimulator of claim 10, wherein said compression member is made of an elastic material.

15. The stimulator of claim 10, wherein said compression member comprises at least one of a compression band or a silicone body integrally molded into said housing of said stimulator.

16. A system comprising:
   a stimulator having an orifice within a housing thereof, said orifice having an opening in communication with an outer surface of said housing; and
   a septum assembly coupled to said stimulator and configured to cover said opening of said orifice;
   wherein said septum assembly comprises
   first and second housing components each defining at least an inner surface, wherein said housing components are made of a generally rigid material and the inner surfaces of the first and second housing components oppose each other,
   a first sealing strip disposed at least partially on said inner surface of said first housing component,
   a second sealing strip disposed at least partially on said inner surface of said second housing component, and
   a compression member at least partially surrounding said housing components, wherein the compression member is configured and arranged to expand in response to a tool inserted between the first and second housing components to further separate the first and second housing components;
   wherein said first and second sealing strips are configured to create a seal over said opening of said orifice.

17. The system of claim 16, wherein said compression member is configured to exert a force on said first and second housing components such that said first and second sealing strips are in contact one with another to create a seal therebetween.

18. The system of claim 16, further comprising a lead extension assembly coupled to said stimulator, wherein said septum assembly is configured to be disposed within said lead extension assembly.

19. The system of claim 16, further comprising a header assembly coupled to said stimulator, wherein said septum assembly is configured to be disposed within said header assembly.

* * * * *